(12) United States Patent
Maleke et al.

(10) Patent No.: US 8,469,891 B2
(45) Date of Patent: Jun. 25, 2013

(54) VISCOELASTICITY MEASUREMENT USING AMPLITUDE-PHASE MODULATED ULTRASOUND WAVE

(75) Inventors: Caroline Maleke, Bellevue, WA (US); Liexiang Fan, Sammamish, WA (US); Kevin Michael Sekins, Yarrow Point, WA (US); Roee Lazebnik, San Jose, CA (US); John Benson, Issaquah, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 7 days.

(21) Appl. No.: 13/029,369

(22) Filed: Feb. 17, 2011

(65) Prior Publication Data

US 2012/0215101 A1 Aug. 23, 2012

(51) Int. Cl.
*A61B 8/00* (2006.01)
*G01N 11/10* (2006.01)
*G01N 29/00* (2006.01)

(52) U.S. Cl.
USPC .............................. 600/438; 73/54.41; 73/602

(58) Field of Classification Search
USPC ................... 600/437, 438; 382/128; 367/124, 367/125; 342/114; 73/54.41, 602, 601; 702/19, 702/66, 142
See application file for complete search history.

(56) References Cited

U.S. PATENT DOCUMENTS

| 5,606,971 | A | 3/1997 | Sarvazyan |
| 5,810,731 | A | 9/1998 | Sarvazyan et al. |
| 6,246,895 | B1 | 6/2001 | Plewes |
| 6,486,669 | B1 | 11/2002 | Sinkus et al. |
| 6,735,461 | B2 | 5/2004 | Vitek et al. |
| 6,879,155 | B2 | 4/2005 | Ehman et al. |
| 7,259,558 | B2 | 8/2007 | Bieri et al. |
| 7,307,423 | B2 | 12/2007 | Ehman et al. |
| 7,414,705 | B2 * | 8/2008 | Boillot ..................... 356/5.01 |
| 7,753,847 | B2 | 7/2010 | Greenleaf et al. |
| 2005/0004466 | A1 | 1/2005 | Hynynen et al. |
| 2007/0276242 | A1 * | 11/2007 | Konofagou ................ 600/437 |
| 2009/0005682 | A1 * | 1/2009 | Fan et al. .................. 600/443 |
| 2010/0160778 | A1 * | 6/2010 | Eskandari et al. ......... 600/438 |
| 2011/0130660 | A1 * | 6/2011 | Cloutier et al. ............ 600/438 |
| 2011/0263978 | A1 * | 10/2011 | Chen et al. ................ 600/438 |

OTHER PUBLICATIONS

Lewa CJ. 1991. Magnetic-Resonance-Imaging in the presence of mechanical waves. *Spectroscopy Letters* 24(1) 55-67.
Lewa CJ. 1994. Elastic properties imaging by periodical displacement nmr measurement (epmri). In *Proceeding of the IEEE Ultrasonics Symposium*, vol. 2, 691-694.
Plewes DB, Betty I, Urchuk SN and Soutar I. 1995. Visualizing tissue compliance with MR imaging. *J Magn Reson Imaging* 5(6) 733-738.
Muthupillai R, Lomas DJ, Rossman PJ, Greenleaf JF, Manduca A and Ehman RL. 1995. Magnetic resonance elastography by direct visualization of propagating acoustic strain waves. *Science* 269 1854-7.

(Continued)

*Primary Examiner* — Long V. Le
*Assistant Examiner* — Katherine Fernandez

(57) ABSTRACT

A viscoelastic property of tissue is measured in vivo. To collect more information and/or estimate viscosity, shear modulus, and/or other shear characteristics, an amplitude and phase modulated waveform is transmitted to the tissue. The displacement caused by the waveform over time includes displacements associated with response to different frequencies. By examining the displacement in the frequency domain, one or more viscoelastic properties may be calculated for different frequencies. The frequency response may indicate the health of the tissue.

15 Claims, 3 Drawing Sheets

OTHER PUBLICATIONS

Muthupillai R, Rossman PJ, Lomas DJ, Greenleaf JF, Riederer SJ and Ehman RL. 1996. Magnetic resonance imaging of transverse acoustic strain waves. *Magn Reson Med* 36 266-74.

Kruse SA, Smith JA, Lawrence AJ, Dresner MA, Manduca A, Greenleaf JF and Ehman RL. 2000. Tissue characterization using magnetic resonance elastography: preliminary result. *Phys Med Biol* 45(6) 1579-1590.

Manduca A, Oliphant TE, Dresner MA, Mahowald JL, Kruse SA, Amromin E, Felmlee JP, Greenleaf JF and Ehman RL. 2001. Magnetic resonance elastography: Non-invasive mapping of tissue elasticity. *Med Image Analysis* 5(4) 237-254.

Sinkus R, Tanter M, Xydeas T, Catheline S, Bercoff J and Fink M. 2005. Viscoelastic shear properties of in vivo breast lesions measured by MR elastography. *Magn Reson Imaging* 23 159-65.

Vappou J, Breton E, Choquet P, Goetz C, Willinger R and Constantinesco A. 2007. Magnetic resonance elastography compared with rotational rheometry for in vitro brain tissue viscoelasticity measurement. *Magn Reson Mater Phys, Biol Med* 20(5-6) 273-278.

Ehman EC, Rossman PJ, Kruse SA, Sahakian AV and Glaser KJ. 2008. Vibration safety limits for magnetic resonance elastography. *Phys Med Biol* 53 925-935.

Hoyt K, Parker KJ, Rubens DJ. 2007. Real-time shear velocity imaging using sonoelastographic techniques. *Ultrasound Med Biol* 33(7):1086-1097.

Pellot-Barakat C, Sridhar M, Lindfors KK, Insana MF. Ultrasonic elasticity imaging as a tool for breast cancer diagnosis and research. Curr. Med. Imaging Rev. 2006;2(1)157-164.

Insana MF, Pellot-Barakat C, Sridhar M, Lindfors KK. Viscoelastic imaging of breast tumor microenvironment with ultrasound. J. Mammary Gland Biol. Neoplasia 2004;9(4):393-404.

Ophir J, Cespedes I, Ponnekanti H, Yazdi Y, Li X. Elastography: A quantitative method for imaging the elasticity of biological tissues. Ultrason. Imaging 1991;13(2):111-134.

Muthupillai R, Lomas DJ, Rossman PJ, Greenleaf JF, Manduca A, Ehman RL. Magnetic-Resonance Elastography by Direct Visualization of Propagating Acoustic Strain Waves. Science 1995;269(5232):1854-1857.

Sandrin L, Fourquet B, Hasquenoph JM, Yon S, Fournier C, Mal F, Christidis C, Ziol M, Poulet B, Kazemi F and others. Transient elastography: A new noninvasive method for assessment of hepatic fibrosis. Ultrasound Med. Biol. 2003;29(12)1705-1713.

Nightingale KR, Palmeri ML, Nightingale RW, Trahey GE. On the feasibility of remote palpation using acoustic radiation force. J. Acoust. Soc. Am. 2001;110(1):625-634.

Nightingale KR, Kornguth KP, Trahey GE. The use of acoustic streaming in breast lesion diagnosis: A clinical study. Ultrasound Med. Biol. 1999;25(1):75-87.

Bercoff J, Tanter M, Fink M. Supersonic shear imaging: A new technique for soft tissue elasticity mapping. IEEE Trans. Ultrason. Ferroelectr. Freq. Control 2004;51(4):396-409.

Sarvazyan AP, Rudenko OV, Swanson SD, Fowlkes JB, Emelianov SY. Shear wave elasticity imaging: a new ultrasonic technology of medical diagnostics. Ultrasound Med Biol 1998;24(9):1419-35.

Fatemi M, Greenleaf JF. Ultrasound-stimulated vibro-acoustic spectrography. Science 1998;280(5360):82-85.

Fatemi M, Greenleaf JF. Vibro-acoustography: An imaging modality based on ultrasound-stimulated acoustic emission. Proc. Natl. Acad. Sci. U. S. A. 1999;96(12):6603-6608.

Konofagou EE, Hynynen K. Localized harmonic motion imaging: Theory, simulations and experiments. Ultrasound Med. Biol. 2003;29(10)1405-1413.

Maleke C, Pernot M, Konofagou EE. A Single-element focused ultrasound transducer method for harmonic motion imaging. Ultrason. Imaging 2006;28(3)144-158.

Maleke C, Luo JW, Gamarnik V, Lu XL, Konofagou EE. A simulation study of amplitude-modulated (AM) Harmonic Motion Imaging (HMI) for early detection and stiffness contrast quantification of tumors with experimental validation. 2010 Ultrason. Imaging (accepted).

Vappou J, Maleke C, Konofagou EE. Quantitative viscoelastic parameters measured by Harmonic Motion Imaging. Phys. Med. Biol. 2009;54(11):3579-3594.

Varghese T, Ophir J. Enhancement of echo-signal correlation in elastography using temporal stretching. IEEE Trans. Ultrason. Ferroel. Freq. Cont. 1997;44:173-180.

Chaplain MAJ, Sleeman BD. Modeling the growth of solid tumors and incorporating a method for their classification using nonlinear elasticity theory. J. Math. Biol. 1993;31(5):431-473.

Fuchsjaeger M, Kolb T, Lichy J, Zuley M, Lenington S, Wagner R. 2002b. The sensitivity and specificity of electrical impedance imaging or carcinoma in women with known breast lesions: The effect of lesion size. Abstract 1237, RSNA 2002, Chicago, IL.

Ophir J, Alam SK, Garra B, Kallel F, Konofagou EE, Krouskop T, Varghese T. Elastography: ultrasonic estimation and imaging of the elastic properties of tissues. Proc. Instn. Mech. Engrs. 1999;213:203-233.

Céspedes I, Ophir J, Ponnekanti H, Maklad N. Elastography: elasticity imaging using ultrasound with application to muscle and breast in vivo. Ultrason. Imaging 1993;15:73-88.

Parker KJ, Huang SR, Musulin RA, Lerner RM. Tissue response to mechanical vibrations for Sonoelasticity Imaging. Ultrasound Med. Biol. 1990;16(3):241-246.

Lerner RM, Huang SR, Parker KJ. "Sonoelasticity" images derived from ultrasound signals in mechanically vibrated tissues. Ultrasound Med. Biol. 1990;16:231-239.

Chen S, Urban MW, Pislaru C, Kinnick R, Zheng Y, Yao A, and Greenleaf JF. Shearwave dispersion ultrasound vibrometry (SDUV) for measuring tissue elasticity and viscosity. IEEE Trans. Ultrason. Ferroelectr. Freq. Control 2009;56(1):55-62.

Michishita K, Hasegawa H, Kanai H. Ultrasonic measurement of minute displacement of object cyclically actuated by acoustic radiation force. Jpn. J. Appl. Phys. Part 1—Regul. Pap. Short Notes Rev. Pap. 2003;42(7A):4608-4612.

Souchon R, Salomir R, Beuf O, Milot L, Grenier D, Lyonnet D, Chapelon JY and Rouviere O. 2008. Transient MR elastography (t-MRE) using ultrasound radiation force: Theory, safety, and initial experiments in vitro. *Magn Reson Med* 60(4) 871-881.

McDannold N, Maier SE. 2008. Magnetic resonance acoustic radiation force imaging. *Med Phys* 35(8) 3748-3758.

Chen J, Watkins R and Pauly KB. 2010. Optimization of Encoding Gradients for MR-ARFI. *Magn Reson Med* 63(4) 1050-1058.

Hertzberg Y, Volovick A, Zur Y, Medan Y, Vitek S, and Navon G. 2010. Ultrasound focusing using magnetic resonance acoustic radiation force imaging: Application to ultrasound transcranial therapy. *Med Phys* 37(6) 2934-2942.

Pauly KB, Kaye E and Chen J. MR-ARFI Sequences for Focal Spot Localization. *2nd International Symposium of MR-guided Focused Ultrasound*, Washington DC, Oct. 17-20, 2010.

Rieke V, Werner B, McDannold N, Grissom W, and Pauly KB. Hybrid Referenceless and Multi-baseline Thermometry for MRgFUS Brain Applications. *2nd International Symposium of MR-guided Focused Ultrasound*, Washington DC, Oct. 17-20, 2010.

Pauly KB, Holbrook A, Santos J, and Ghanouni P. Focused Ultrasound of the liver during free breathing. *2nd International Symposium of MR-guided Focused Ultrasound*, Washington DC, Oct. 17-20, 2010.

M. Fatemi, et al., "Probing the dynamics of tissue at low frequencies with the radiation force of ultrasound", Phys. Med. Biol. 45 (2000), IOP Publishing Ltd., UK, pp. 1449-1464.

\* cited by examiner

VISCOELASTICITY MEASUREMENT USING AMPLITUDE-PHASE MODULATED ULTRASOUND WAVE

BACKGROUND

The present embodiments relate to viscoelasticity measurements. In particular, a viscoelastic property of tissue is measured in vivo.

Shear modulus characteristics of a tissue sample may be measured with a rheometer. A rheometer is a mechanical device capable of subjecting a sample to either a dynamic (e.g., sinusoidal) or static (e.g., linear) deformation. The rheometer may measure the storage shear modulus and the loss shear modulus for a frequency range. The range is limited based on material stiffness, such as 1 to 10 Hz for soft tissue. For medical use, tissue is extracted from a patient for placement in the rheometer. The rheometer is not used for in vivo measurements. The measurements depend on the size and shape of the extracted tissue sample, as well as boundary conditions due to the extraction.

Shear characteristics may be measured in vivo with ultrasound. For example, shear velocity detection is used in various diagnostic applications, such as assessing liver disease. For shear wave detection, an ultrasound pushing pulse (e.g., a one cycle pulse) is fired along a scan line. The pushing pulse generates a shear wave, causing displacement of tissue. The displacement is measured. To detect the shear wave velocity, multiple pushing pulses along a same scan line and corresponding displacement detection scans are used. These shear measurements may have limited information or depend on the compression level.

BRIEF SUMMARY

By way of introduction, the preferred embodiments described below include methods, instructions, and systems for measuring a viscoelastic property of soft tissue in vivo. To collect more information and/or estimate viscosity, shear modulus, and/or other shear characteristics, an amplitude and phase modulated waveform is transmitted to the tissue. The displacement caused by the waveform over time includes displacements associated with response to different frequencies. By examining the displacement in the frequency domain, one or more viscoelastic properties may be calculated for different frequencies. The frequency response may indicate the health of the tissue.

In a first aspect, a non-transitory computer readable storage medium has stored therein data representing instructions executable by a programmed processor for measuring a viscoelastic property of tissue in vivo. The storage medium includes instructions for transmitting an amplitude modulated and phase modulated waveform including cycles at different frequencies at different times, the different frequencies being in a range of frequencies, the amplitude modulated and phase modulated waveform transmitted to the tissue in a patient, calculating displacement as a function of time of the tissue in response to the amplitude modulated and phase modulated waveform, the displacement calculated from scans of the tissue, applying a Fourier transform to the displacement over time; and determining the viscoelastic property from a Fourier transform of a shear wave equation and the Fourier transform of the displacement over time.

In a second aspect, a method is provided for viscoelastic measurement using ultrasound. An amplitude and phase modulated ultrasound waveform is transmitted into a patient in vivo. A viscoelastic property is measured from shear caused by the amplitude and phase modulated ultrasound waveform. The viscoelastic property is measured over a range of frequencies associated with the amplitude and phase modulated ultrasound waveform and independent of an amount of compression applied externally to the patient during the transmitting.

In a third aspect, a system is provided for shear wave calculation using ultrasound. A transmit beamformer is operable to generate an amplitude and phase modulated waveform. An ultrasound transducer is connected with the transmit beamformer such that the ultrasound transducer transmits acoustic energy to tissue in a patient in response to the amplitude and phase modulated waveform. A receive beamformer is operable to output data representing spatial locations as a function of received acoustic signals. A processor is configured to estimate displacement of the tissue over time as a function of the output data and to calculate shear information as a function of the displacement of the tissue over time. A display is operable to display an image, which is a function of the shear information.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Tissue mechanical properties are measured in vivo. The properties of any structure or material in a patient, such as soft tissue, may be measured. An amplitude modulated (AM) and phase modulated (PM) ultrasound waveform causes tissue displacement. The one AM-PM waveform produces a vibration at successive frequencies inside the patient at a desired tissue. Tissue shear modulus and viscosity are measured at various frequencies with this one excitation, allowing measurement in less than two seconds. Phase modulation at lower frequencies (e.g., 1-100 Hz) may provide a higher signal-to-noise ratio. The AM-PM waveform allows collection of information during or after inducement of the shear.

A fast and reliable method may assess material stiffness for various frequencies in a single measurement. By collecting measurements for different frequencies, the resulting knowledge of material (e.g., tissue) mechanical properties may complement diagnostic procedures. The knowledge may include quantitative parameters, such as strain, viscosity, and/or shear modulus. The quantitative parameters are independent of the amount of compression applied to the tissue as the parameters are derivatives of displacement. The frequency response may be independent of compression. The knowledge may include qualitative parameters, such as displacement. The displacement may depend on an amount of pressure applied at the tissue. The knowledge may include derived information. The slope of the shear modulus vs. frequency and/or the slope of the viscosity vs. frequency may provide information pertaining to tissue mechanical property related to tissue pathology. The slopes are independent of pre-compression levels. The measurements may be repeated to increase accuracy. Since the measurements do not rely on contact, the measurements are independent of boundary condition, material size, and shape.

Figure 1:
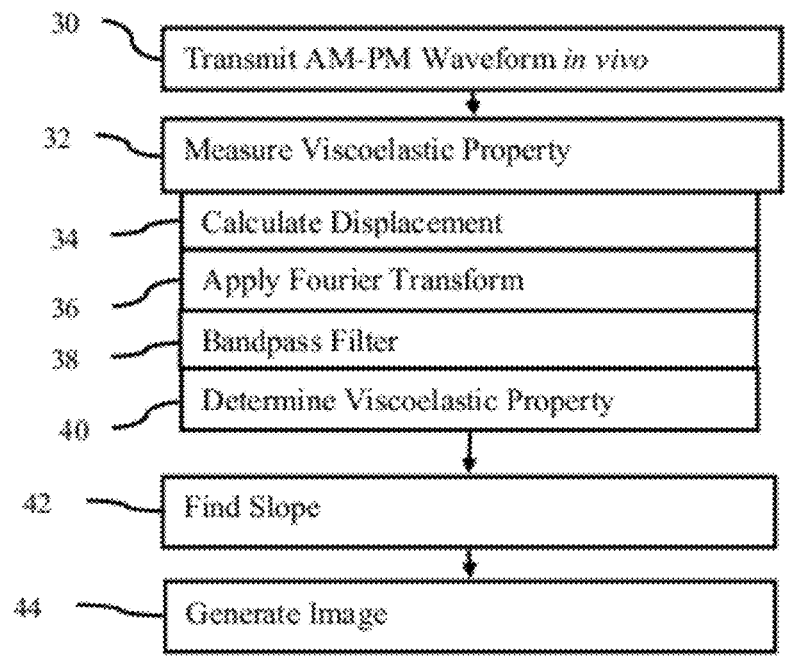
FIG. 1 is a flow chart diagram of one embodiment of a method for measuring a viscoelastic property of tissue in vivo.

FIG. 1 shows a method for viscoelastic measurement using ultrasound. An ultrasound transmission is used to generate tissue displacement in response to different frequencies. In this way, ultrasound is used to calculate a viscoelastic property. The method is implemented by the system of FIG. 6 or a different system. Additional, different, or fewer acts may be provided. For example, the method is performed without acts 38, 42, and/or 44. As another example, act 32 is performed without one or more of acts 34-40. The acts are performed in the order described or shown, but may be performed in other orders.

In act 30, an amplitude modulated and phase modulated waveform is transmitted. An ultrasound transducer transmits an acoustic waveform converted from an electrical waveform. The acoustic energy with the amplitude modulated and phase modulated waveform is transmitted to the tissue in a patient. The transmission occurs in vivo.

The acoustic waveform is transmitted for generating a shear wave. The excitation is an ultrasound pushing pulse. The acoustic energy is focused, resulting in one or more beams for each transmission. The excitation is focused using a phased array and/or mechanical focus. The excitation is focused at a location to allow detecting of the resulting shear wave, such as focused at a tissue location surrounding and/or including a possible tumor.

Figure 2:
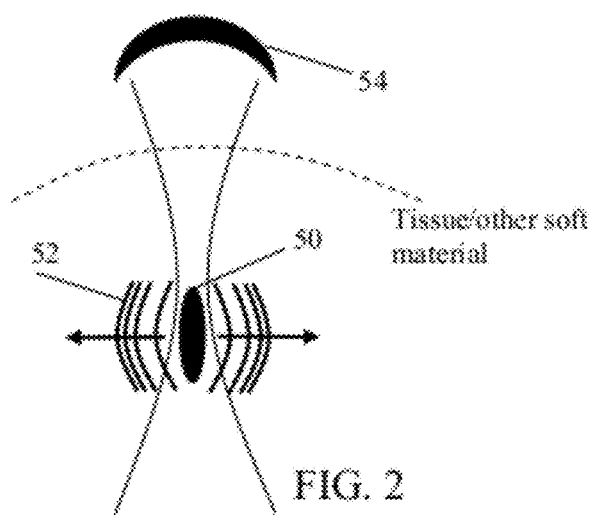
FIG. 2 is a graphic illustration of a shear inducing ultrasound transmission.

As represented in FIG. 2, the shear wave 52 is generated at the focal region 50 by the transducer 54 and propagates laterally from the focal region 50. The arrows are shown in one direction (e.g., horizontally), but the shear wave travels in multiple directions. The shear wave reduces in amplitude as the wave travels through the tissue.

To generate the shear wave, high amplitude or power excitations are desired. For example, the excitation has a mechanical index of close to but not exceeding 1.9. To be conservative and account for probe variation, mechanical index of 1.7 or other level may be used as the upper limit Greater (e.g., MI exceeding 1.9) or lesser powers may be used. Transmitting along the same or adjacent scan lines may cause the tissue to increase in temperature over time. Biological effects may include hyperthermia at tissue temperature of about 41-45° C., protein denaturation at temperatures above 43-45° C., and tissue necrosis at temperatures above 50° C. Tissue stiffness may be affected even at temperatures below 43-45° C. At temperatures above 43-45° C., increases in viscosity and/or stiffness may occur. At temperatures above 50° C., the tissue may have a high stiffness and/or high attenuation. Biological effects are limited by preventing a temperature increase of over 2 degrees Celsius. Alternatively, the transmissions may cause biological effects.

The electrical and corresponding acoustic waveforms include cycles at different frequencies at different times. The different frequencies are in a range of frequencies. The frequency range may be optimized based on the type of tissue being examined. For example, breast tissue may have a maximum displacement response at 50 Hz, so the range includes 50 Hz. As another example, tumors may be harder than soft tissue, so have a greater frequency at which maximum displacement response occurs. For tumor measuring, the frequency range may be greater. In one embodiment, the frequency range is within 15 to 75 Hz for the phase modulation.

Figure 3:
FIG. 3 illustrates an example amplitude and phase modulated waveform.

Any frequency variation function may be used for the phase modulation. For example, a chirp frequency sweep within the range is used. FIG. 3 shows a waveform with an amplitude and phase modulated envelope. The phase modulate begins at the lowest frequency and sweeps or gradually changes to the highest frequency in the range. Other frequency variation may be used, such as nonlinear, random, or other steps between the different frequencies in any order.

The amplitude modulation is any function. The amplitude modulation separates individual frequencies or groups of frequencies from each other.

In one embodiment, the amplitude and phase modulated waveform is generated by multiplying a sinusoidal carrier (in MHz range) by a sinusoidal amplitude modulation with a phase varying term (in Hz range). The amplitude modulation with the phase varying term defines an envelope with amplitude and phase modulation. The waveform may be represented as:

$$x(t)=A\sin(\omega_c t)\times\sin((\omega_m+\Delta\omega_m t)t)$$

where x(t) is the waveform as a function of time, A is an amplitude weight, $\omega_c$ is a center frequency or carrier frequency, and $\Delta\omega_m$ is a modulation frequency which changes over time. In one embodiment, $\omega_m+\Delta\omega_m$ varies within 15 to 75 Hz, but other ranges may be used. FIG. 3 shows a waveform with the 15-75 Hz range.

The waveform has any number of envelope and carrier cycles. In one embodiment, the waveform has sufficient cycles to be 1333 milliseconds, but greater or less lengths of time may be used. The number of cycles of the carrier is tens, hundreds, thousands, or more. The number of cycles of the envelope or modulation is two or more.

The tissue response is a function of the waveform, x(t) and the tissue characteristics. The displacement, y(t), of the tissue over time may be expressed as a convolution of the waveform, x(t) and the tissue characteristics or response, h(t): y(t)=x(t)*h(t). The tissue response reflects viscoelastic properties of the tissue.

One or more viscoelastic properties are measured from shear caused by the amplitude and phase modulated ultrasound waveform in act 32. In order to measure the viscoelastic properties in act 32, the displacement, y(t), of the tissue over time in response to the amplitude and phase modulated waveform is measured in act 34. Act 32 is shown as including acts 34, 36, 38, and 40. Different, additional, or fewer acts may be provided. In other embodiments, other processes are used to measure the viscoelastic property.

In act 34, the displacement is calculated as a function of time. The tissue is scanned multiple times to determine the displacement, such as scanning a region at least three times to determine displacement at two different times.

The displacement of the tissue is in response to the amplitude modulated and phase modulated waveform. The displacement of the tissue caused by the shear wave is determined over time. As the shear wave passes a given location, the tissue displaces by an amount or distance that increases to a peak amount and then decreases as the tissue returns to rest. Since the AM-PM waveform includes many cycles, the tissue may continuously be displaced. The amplitude modulation causes variance in the displacement over time as the tissue begins to return to a normal state as the amplitude decreases. The phase modulation results in variation of the amount of displacement over time.

The tissue is scanned using any imaging modality capable of scanning for displacement during the tissue's response to the pushing waveform, such as during or after application of the AM-PM waveform. The scan occurs before the tissue returns to a relaxed or normal state or position, but may include scans of the tissue at times where the tissue has returned to rest. Ultrasound and magnetic resonance imaging are two possible modalities from calculating displacement from scans of the tissue.

For ultrasound scanning, the shear wave 52 is detected at locations adjacent to and/or spaced from the focal region for the AM-PM waveform. To detect the displacement, ultrasound energy is transmitted to the tissue undergoing displacement, and reflections of the energy are received. To detect tissue response to shear waves in a region of interest, transmissions are made to other focal regions, and detection is performed around the other focal regions. These other transmissions are for detecting the shear waves rather than causing the shear wave. The transmissions for detection may have lower power and/or short pulses (e.g., 1-5 carrier cycles) and use the same or different scan line as the AM-PM waveform. The transmissions for detection may have a wider beam profile along at least one dimension, such as laterally, for simultaneously forming receive samples along a plurality of scan lines. The shear wave may be monitored in one, two, or more directions.

A region of interest is monitored to detect the shear wave. The region of interest is any size, such as 6 mm in lateral and 10 mm in axial surrounding the focal location of the AM-PM waveform. This detection region is monitored by ultrasound. For example, B-mode scans are performed to detect tissue displacement caused by the shear wave. Doppler, color flow, or other ultrasound mode may be used to monitor for the shear wave.

The monitoring is performed for any number of scan lines. For example, four receive beams are formed in response to each transmission. After transmitting the excitation to generate the shear wave, B-mode transmissions are performed repetitively along one or more transmit scan lines and receptions along corresponding receive scan lines. In other embodiments, only a single receive beam or other numbers of receive beams are formed in response to each transmission. Some of the ultrasound data, such as at the beginning or end of the repetitions, may not be responsive to the shear wave.

The transmission and reception for detection are performed multiple times to determine change due to displacement over time. Any transmission and reception sequence may be used. The detection of displacement may be interleaved with other scanning, such as scanning different regions for displacement separately.

Figure 4:
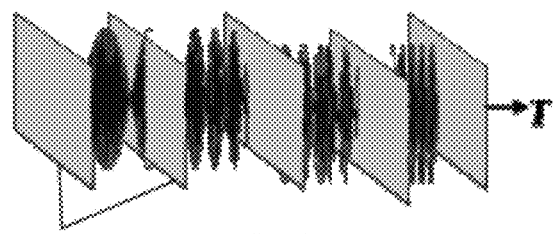
FIG. 4 shows one embodiment of scans for displacement detection relative to the amplitude and phase modulated waveform of FIG. 3.

The transmission and reception for detection are interleaved with the amplitude and phase modulated waveform. For example, the transmission(s) and reception(s) for scanning a region once are performed each time the amplitude modulation is at or near a zero level. As another example, the scanning of the tissue is interleaved with the transmitting of act 30 on a periodic basis, such as every 1.67 milliseconds. The interleaving avoids interference, such as the amplitude and phase modulation waveform being halted during the scanning so that echoes from the waveform are minimized. FIG. 4 shows an example of interleaving scans of the planes 56 with the amplitude and phase modulated waveform. The interleaving period may be more or less frequent. When the amplitude and phase modulation continues after halting for the displacement scan, the waveform begins from a point in the waveform where the transmission ceased. In alternative embodiments, the scanning is done at a different frequency or with different coding than the amplitude and phase modulated waveform. Both the pushing waveform and the scanning may occur simultaneously, and frequency or coding is used to distinguish echoes from each.

The discussion above is for one depth or location. The viscoelastic property is measured for one location. To monitor a larger region, acts 30-40 are repeated for other locations. For each receive beam location, a time profile of motion information is provided, represented by the ultrasound data. A separate time profile is provided for each axial depth as well as lateral location.

The displacement is calculated from the ultrasound scan data. The tissue moves between two scans. The data of one scan is translated in one, two, or three dimensions relative to the data in the other scan. For each possible relative position, an amount of similarity is calculated. The amount of similarity is determined with correlation, such as a cross-correlation. A minimum sum of absolute differences or other function may be used. The spatial offset with the highest or sufficient correlation indicates the amount and direction of displacement.

Displacements are determined for a given location at different times, such associated with sequential scans. The displacement is determined with respect to an initial or reference frame of scan data (i.e., cumulative displacement). Alternatively, the displacement is determined from the immediately prior frame of scan data, such assigning the previous frame as the reference on an ongoing basis (i.e., incremental displacement). The temporal profile for a given location indicates displacement caused by the shear wave over time and in response to different portions of the amplitude and phase modulated waveform.

Figure 5:
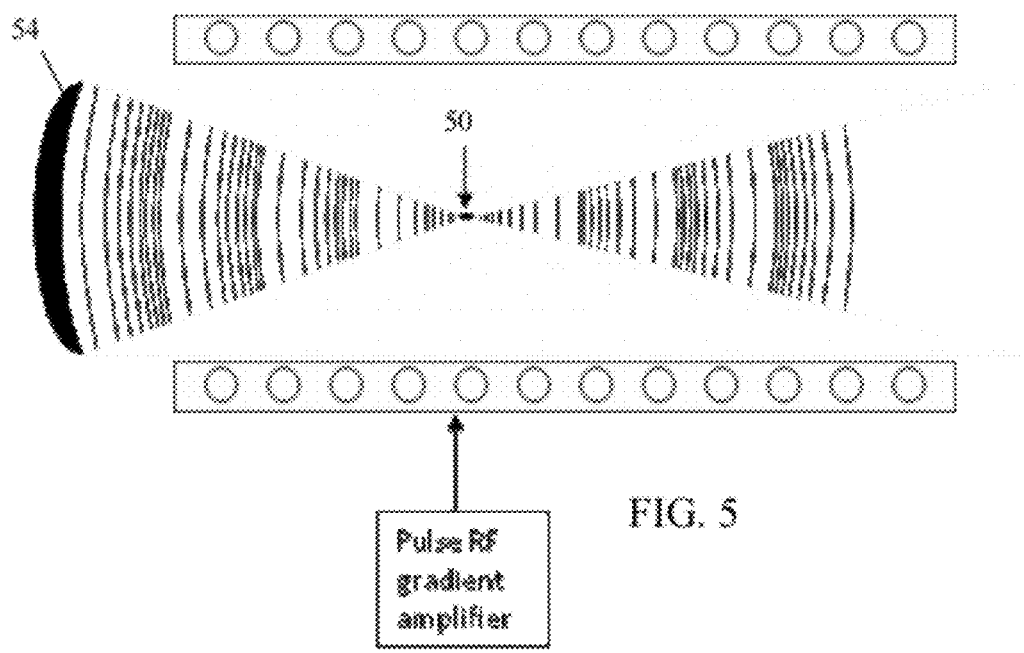
FIG. 5 illustrates relative locations of a transducer for causing shear wave propagation within the targeted tissue and radio frequency coils for measuring displacement in an example magnetic resonance embodiment.

For scanning with magnetic resonance, a similar process is used. FIG. 5 shows the transducer 54 transmitting to a focal region surrounded, at least in part, by a magnetic resonance bore. The bore includes radio frequency coils. A uniform magnetic field is generated. Using a pulse radio frequency gradient amplifier, the spins of the molecules in the patient are altered. The coils are used to detect the alteration, acquiring k-space data.

Rather than correlate between frames in a sequence, a set of displacement data over time is acquired. K-space magnetic resonance data representing the tissue of the patient is acquired at different times or in a sequence. One set (reference set) is acquired without the tissue subjected to the amplitude and phase modulated waveform. Another set is acquired during application of the amplitude and phase modulated waveform. Since the ultrasound of the waveform does not interfere with the k-space data, the scan data may be acquired without interleaving. Alternatively, interleaving is used. The sequence of scanning is periodic (e.g., every 1.67 ms), based on the low amplitude portions of the amplitude modulated waveform, or another function.

The k-space data is acquired in synchronization with one or more physiological cycles, such as the heart or breathing cycle. The scans of the reference sequence are acquired at the same points in the cycle as the displacement set. While k-space data may be used without processing into an image, image data is used in alternative embodiments.

The reference magnetic resonance data representing the tissue free of responding to the transmitting is subtracted from the magnetic resonance data representing the tissue response to the transmitting. Alternatively, the data representing the tissue response is subtracted from the reference data. The scans from similar times relative to the physiological cycle are subtracted. The subtraction isolates differences. Since the shear wave causes a difference, the offset or displaced tissue remains and the other signals cancel from the subtraction.

After low pass filtering or other processing, the amount, direction, or amount and direction of the displacement between sequential frames is determined. A location of a peak intensity point or region is identified in the data for each frame of subtraction data. The difference in locations between sequential frames or between a different frame and a reference frame is calculated as the displacement. The displacement varies over time due to the differences in the amplitude and phase modulated waveform applied at the different times.

In act 36, the displacement over time is transformed into the frequency domain. A Fourier transform is applied to the displacement over time. Any transform may be used. Since the displacement over time is responsive to different frequencies of the amplitude and phase modulated waveform, the transform into the frequency domain provides different response levels as a function of frequency. The Fourier transform of the displacement, y(t), may be represented as Y(Ω), where Ω is the frequency, i.e., representation of displacement in the frequency domain.

The transform of the displacement or tissue response is represented as:

$$h(t) \xleftrightarrow{FT} H(\Omega) = \frac{Y\Omega}{X\Omega}$$

In act 38, the displacement in the frequency domain is filtered. Any filtering may be used, such as band pass filtering. The frequency range of the band pass filter is set based on the frequency range of the transmitted amplitude and phase modulated waveform. The acoustic force is a function of the square of the pressure. As a result, the displacement or vibration induced by the waveform is twice the frequency of the waveform. For example, the waveform includes frequency variation of the envelope from 15 to 75 Hz, so the responsive displacement information occurs at 30 to 150 Hz. The width of the frequency range is twice the range of the waveform, and the low and high frequencies in the range are twice the low and high frequencies of the range of the waveform. The filtering isolates the information in this range or a sub-range. Frequency data outside the range is not used and data within the range is used, resulting in band pass filtering. Other band pass filtering, other filtering, other processing, or no data modification processes may be used.

In act 40, the viscoelastic property is determined from the Fourier transform of the displacement over time. The shear wave may be represented as:

$$\frac{\partial^2 y_z}{\partial t^2} - c_s^2 \Delta y_z = 0$$

$$\frac{\partial^2 y_z}{\partial t^2} - \left(\mu + \eta \frac{\partial}{\partial t}\right) \Delta y_z = 0$$

Other shear wave representations may be used.

In the frequency domain, the shear wave equation is represented as:

$$\frac{-\omega^2 Y(\Omega)}{\Delta Y(\Omega)} = \mu - \eta \omega j$$

This equation represents the Fourier transform of the shear wave equation. Other representations may be used, depending on the shear wave representation and Fourier transform used. The terms of the left side of the equation are known or measured, such as the resulting motion (displacement) in frequency domain, Y(Ω), that oscillates at frequency (ω) equal to twice the AM-PM frequency, e.g., 2×(15 to 75 Hz)=30 Hz to 150 Hz. The right side represents the imaginary and real portions of the transformed shear wave equation.

The viscoelastic property is determined from the shear wave equation in the frequency domain. Any modulus, viscosity, or shear value may be estimated. Tissue modulus values represent the hardness or stiffness of the tissue. For example, the shear modulus of tissue is estimated. In alternative embodiments, Young's modulus is estimated. In other embodiments, other shear values are estimated, whether quantitative or qualitative.

In one embodiment, viscosity is determined. The viscosity is calculated as a function of results of the applying of the Fourier transform. The imaginary part of the Fourier transform of the shear wave equation may be used to determine viscosity. The imaginary part is divided by the frequency, ω, to provide viscosity. This is represented as:

$$\eta = \frac{\text{Im}\left\{\frac{-\omega^2 y(\Omega)}{\Delta Y(\Omega)}\right\}}{\omega}$$

In an alternative or additional embodiment, the shear modulus is determined. The shear modulus is calculated as a function of the results of applying the Fourier transform. The real part of the Fourier transform of the shear wave equation may be used to determine the shear modulus. The real part itself represents the shear modulus. This is represented as:

$$\mu = \text{Re}\left\{\frac{-\omega^2 y(\Omega)}{\Delta Y(\Omega)}\right\}$$

The viscoelastic property, such as the viscosity or shear modulus, may be determined over a range of frequencies (ω). For example, the displacement data is within the 30 to 150 Hz range. The viscosity is determined over the same range. The viscosity for groups of frequencies or for sub-bands may be averaged, such as providing values for every 5 Hz. The property is determined in response to only the amplitude modulated and phase modulated waveform and scans of the tissue during application of the waveform. Sequential performance of acts 30-40 is not provided, but may be. By using one waveform with a range of frequencies, the frequency related response of the tissue may be measured during a short time period, such as sufficient to interleave the scans and the transmission of the waveform.

The viscosity and shear modulus are quantitative properties. The values are independent of an amount of compression applied. The pressure to the patient during the transmitting from the acoustic waveform or from an external source is not needed to determine quantitative properties. In alternative embodiments, a qualitative property is used, such as the displacement.

In act 42, the slope of the viscoelastic property as a function of frequency is found. The property as a function of frequency may be plotted, at least over a portion or the entire range of frequencies (e.g., 30-150 Hz). A line is fit to the plot or data, providing a slope. For example, the slopes of the shear modulus and the viscosity as a function of frequency are determined.

The slope may indicate the health of tissue or assist in diagnosis. For example, healthy tissue may have a more horizontal viscosity slope than a tumor. The frequency response of the tissue may indicate the health or not of tissue. Other functions of the property as a function of frequency may be calculated, such as the variance, amount of change, or curvature.

In act 44, an image is generated. The image represents the property. A numerical or textual indication of the property at a given frequency or calculated from data over different frequencies may be displayed. In other embodiments, the plot and/or line fit and slope value are output. The viscoelastic property is communicated to the user in the image. The image may be a graph, such as a plot of values as a function of frequency.

The image may additionally include a one, two, or three-dimensional representation of the property or other shear information as a function of space or location. For example, the shear velocity throughout a region is displayed. The shear velocity modulates color for pixels in a region in a gray-scale modulated B-mode image. The image may represent displacement information, such as shear or moduli (e.g., the shear moduli) for different locations. The display grid may be different from the scan grid and/or grid for which displacements are calculated. Color, brightness, luminance, hue, or other characteristic is modulated as a function of the shear information.

The acts are repeated for other scan lines and/or other depths. For example, acts 30-40 are performed again for each location in a one, two, or three-dimensional region.

Figure 6:
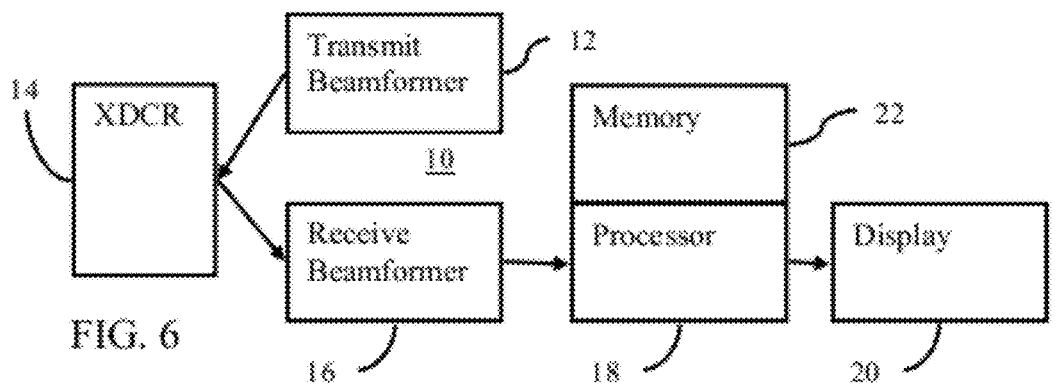
FIG. 6 is one embodiment of a system for shear wave calculation using ultrasound.

FIG. 6 shows one embodiment of a system 10 for shear wave calculation using ultrasound. Ultrasound generates a shear wave, and scan data responsive to the tissue responding to the ultrasound is used to determine a property. The system 10 implements the method of FIG. 1 or other methods. The system 10 includes a transmit beamformer 12, a transducer 14, a receive beamformer 16, an image processor 18, a display 20, and a memory 22. Additional, different or fewer components may be provided. For example, a user input is provided for manual or assisted designation of a region of interest for which shear information is to be obtained. As another example, an additional HIFU transducer is provided for treating the tissue. The system 10 is a medical diagnostic ultrasound imaging system.

In alternative embodiments, the system 10 is a personal computer, workstation, PACS station, or other arrangement at a same location or distributed over a network for real-time or post acquisition imaging.

In yet other alternative embodiments, the system 10 is part of a magnetic resonance system. For example, the transmit beamformer 12 and transducer 14 are provided for transmitting the waveform to generate the shear wave, but the receive beamformer is not provided. Instead, magnetic resonance coils and magnets, such as shown in FIG. 5, are provided with the processor 18, memory 22 and display 20 for scanning.

The transmit beamformer 12 is an ultrasound transmitter, memory, pulser, analog circuit, digital circuit, or combinations thereof. The transmit beamformer 12 is operable to generate waveforms for a plurality of channels with different or relative amplitudes, delays, and/or phasing. Upon transmission of acoustic waves from the transducer 14 in response to the generated waves, one or more beams are formed. The waveforms are each an amplitude and phase modulated waveform, but with relative delays and apodization to provide the desired acoustic waveform (e.g., see FIG. 3) at the focal region.

For scanning tissue displacement, a sequence of transmit beams are generated to scan a one, two or three-dimensional region. Sector, Vector®, linear, or other scan formats may be used. The same region is scanned multiple times, such as represented in FIG. 4. The scanning by the transmit beamformer 12 is interleaved or synchronized with the transmission of the amplitude and phase modulated waveform by the transmit beamformer 12. The same elements of the transducer 14 are used for both scanning and generating shear waves, but different elements, transducers, and/or beamformers may be used.

The transducer 14 is a 1-, 1.25-, 1.5-, 1.75- or 2-dimensional array of piezoelectric or capacitive membrane elements. Alternatively, a single element with a mechanical focus is provided. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. The transducer 14 transmits acoustic energy with an amplitude and phase modulated waveform. The waveform is focused at a tissue region or location of interest in the patient. The acoustic waveform is generated in response to applying the electrical waveform to the transducer elements.

For scanning with ultrasound to detect displacement, the transducer transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for detection. The receive beamformer 16 outputs data representing spatial locations using the received acoustic signals. Relative delays and/or phasing and summation of signals from different elements provide beamformation. In alternative embodiments, the receive beamformer 16 is a processor for generating samples using Fourier or other transforms.

The receive beamformer 16 may include a filter, such as a filter for isolating information at a second harmonic or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or other band.

The receive beamformer 16 outputs beam summed data representing spatial locations. Data for a single location, locations along a line, locations for an area, or locations for a volume are output. Dynamic focusing may be provided. The data may be for different purposes. For example, different scans are performed for B-mode or tissue data than for shear wave detection. Alternatively, the B-mode data is also used to determine displacement caused by a shear wave.

The processor 18 is a B-mode detector, Doppler detector, pulsed wave Doppler detector, correlation processor, Fourier transform processor, application specific integrated circuit, general processor, control processor, image processor, field programmable gate array, digital signal processor, analog circuit, digital circuit, combinations thereof or other now known or later developed device for detecting and processing information from beamformed ultrasound samples.

In one embodiment, the processor 18 includes one or more detectors and a separate processor. The separate processor is a control processor, general processor, digital signal processor, application specific integrated circuit, field programmable gate array, network, server, group of processors, data path, combinations thereof or other now known or later developed device for determining displacement, and calculating tissue properties. For example, the separate processor performs any combination of one or more of the acts shown in FIG. 1. The processor 18 is configured by software and/or hardware to perform the acts.

In one embodiment, the processor 18 estimates tissue displacement over time as a function of the output data from the receive beamformer 16. The displacements are estimated as a profile or data representing a curve of magnitude of displacement as a function of time. The displacement profile may be obtained by correlating or otherwise determining level of similarity between reference data and data obtained during or interleaved with transmission of the amplitude and phase modulated pushing waveform.

The processor 18 is configured to transform the displacement of the tissue over time into the frequency domain. A Fourier transform, such as the Fast Fourier transform, is applied to the displacement data.

The processor 18 is configured to calculate shear information as a function of the displacement of the tissue over time. For example, a shear velocity is calculated from the displacement over time. The amount of displacement divided by the time provides velocity. In one embodiment, the processor 18 calculates viscosity as a function of frequency or at a frequency. The viscosity is calculated from displacement in the frequency domain. The transformed displacement is used to determine viscosity as a function of frequency. The frequencies are in a range associated with the amplitude and phase modulated waveform. The viscosity at one frequency, an average viscosity, or viscosities at different frequencies are calculated in the frequency domain using a representation of shear, but may alternatively be calculated in the time domain. The processor 18 may calculate other properties, such as shear modulus.

The processor 18 generates and outputs image or display values mapped from the viscoelastic property to the display 20. For example, the shear viscosity, shear modulus, or other value is determined. A text or numerical indication of the property is displayed to the user. A graph of viscosity or other property over time or frequency may be displayed. In one embodiment, the processor 18 fits a straight line to the property as a function of frequency and the slope is displayed as a value or graphically.

In additional or alternative embodiments, shear information is displayed as a function of location. The magnitude of shear values modulates the color, hue, brightness, and/or other display characteristic for different pixels representing a tissue region. The processor 18 determines a pixel value (e.g., RGB) or a scalar value converted to a pixel value. The image is generated as the scalar or pixel values. The image may be output to a video processor, look-up table, color map, or directly to the display 20.

The processor 18 operates pursuant to instructions stored in the memory 22 or another memory. The instructions configure the processor 18 for operation by being loaded and/or executed. The processor 18 is programmed for measuring a viscoelastic property of tissue in vivo. The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

The display 20 is a CRT, LCD, projector, plasma, or other display for displaying two-dimensional images or three-dimensional representations. The display 20 displays one or more images representing shear information. The image is a graph, a number, text, and/or two-dimensional representation of a region. For example, a viscosity value or graph of viscosity as a function of frequency is displayed as the image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. In a non-transitory computer readable storage medium having stored therein data representing instructions executable by a programmed processor for measuring a viscoelastic property of tissue in vivo, the storage medium comprising instructions for:

transmitting an amplitude modulated and phase modulated waveform including carrier cycles at different frequencies at different times, the different frequencies being in a range of frequencies, the amplitude modulated and phase modulated waveform comprising a sinusoidal carrier multiplied by a sinusoidal amplitude modulation with a phase varying term such that an envelope of the sinusoidal amplitude modulation includes at least two envelope cycles with each of the envelope cycles separating the sinusoidal carrier at the different frequencies or groups of the different frequencies, the amplitude modulated and phase modulated waveform transmitted to the tissue in a patient;

calculating displacement as a function of time of the tissue in response to the amplitude modulated and phase modulated waveform, the displacement calculated from scans of the tissue, the calculating displacement comprising scanning the tissue with ultrasound interleaved with the transmitting, the interleaving synchronized with the envelope;

applying a Fourier transform to the displacement over time; and determining the viscoelastic property from a Fourier transform of a shear wave equation and the Fourier transform of the displacement over time.

2. The computer readable storage medium of claim 1 wherein the amplitude modulated and phase modulated waveform comprises a chirp frequency sweep within the range.

3. The computer readable storage medium of claim 1 wherein calculating displacement comprises calculating displacement of the tissue between the scans as a function of correlation between data from the scans.

4. The computer readable storage medium of claim 1 wherein applying the Fourier transform comprises transforming the displacement over time into a frequency domain where the displacement at the different times is responsive to the different frequencies.

5. The computer readable storage medium of claim 1 wherein determining the viscoelastic property comprises determining viscosity.

6. The computer readable storage medium of claim 1 wherein transmitting and determining comprises determining the viscoelastic property over the range of frequencies in response to only the amplitude modulated and phase modulated waveform and scans of the tissue during application of the waveform.

7. The computer readable storage medium of claim 1 wherein determining comprises determining both viscosity as a function of an imaginary part and shear modulus as a function of a real part of the Fourier transform of the shear wave equation.

8. The computer readable storage medium of claim 1 further comprising finding a slope of the viscoelastic property as a function of frequency in the range.

9. The computer readable storage medium of claim 1 further comprising band pass filtering the output of application of the Fourier transform of the displacement over time, the band pass being about twice the range of the frequencies in width.

10. A method for viscoelastic measurement using ultrasound, the method comprising:

transmitting an amplitude and phase modulated ultrasound waveform into a patient in vivo, the amplitude modulate and phase modulated waveform comprising a sinusoidal carrier multiplied by a sinusoidal amplitude modulation with a phase varying term such that an envelope of the sinusoidal amplitude modulation includes at least two envelope cycles with each of the envelope cycles separating the sinusoidal carrier at the different frequencies or groups of the different frequencies; and measuring a viscoelastic property from shear caused by the amplitude and phase modulated ultrasound waveform, the viscoelastic property measured over a range of frequencies associated with the amplitude and phase modulated ultrasound waveform and independent of an amount of compression applied externally to the patient during the transmitting, the measuring comprising scanning the tissue with ultrasound interleaved with the transmitting, the interleaving synchronized with the envelope.

11. The method of claim 10 wherein transmitting comprises multiplying the sinusoidal carrier at an ultrasound frequency with the envelope having the amplitude and phase modulation such that the range of frequencies is within 15 Hz to 75 Hz.

12. The method of claim 10 wherein measuring comprises calculating displacement, caused by the transmitting, of tissue of the patient between scans of the scanning, the calculating being as a function of correlation between data from the scans.

13. The method of claim 10 wherein measuring comprises applying a Fourier transform to data representing displacement as a function of time and calculating viscosity as a function of results of the applying of the Fourier transform.

14. The method of claim 13 wherein calculating comprises calculating as a function of an imaginary part of a Fourier transform of the shear wave equation.

15. The method of claim 10 further comprising finding a slope of the viscoelastic property as a function of frequency in the range.

* * * * *